(12) United States Patent
Bustamante et al.

(10) Patent No.: US 8,541,616 B2
(45) Date of Patent: Sep. 24, 2013

(54) ADDITION OF A METHYL HYDROGEN TEREPHTHALATE REACTOR TO A DIMETHYL TEREPHTHALATE PROCESS

(75) Inventors: Laura Ellen Bustamante, Kingsport, TN (US); William Lee Cook, Kingsport, TN (US); Brent Alan Tennant, Kingsport, TN (US); Ashfaq Shaikh, Kingsport, TN (US); Joseph Luther Parker, Kingsport, TN (US); Richard Andrew Virost, Jonesborough, TN (US); Michael Visneski, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 378 days.

(21) Appl. No.: 12/691,136

(22) Filed: Jan. 21, 2010

(65) Prior Publication Data
US 2010/0210867 A1 Aug. 19, 2010

Related U.S. Application Data

(60) Provisional application No. 61/152,277, filed on Feb. 13, 2009.

(51) Int. Cl.
*C07C 67/48* (2006.01)

(52) U.S. Cl.
USPC ............................................................ 560/78

(58) Field of Classification Search
USPC .................................................. 560/77, 78, 98
See application file for complete search history.

(56) References Cited

U.S. PATENT DOCUMENTS

| 3,839,414 A | 10/1974 | Windle, III |
| 4,096,340 A | 6/1978 | Fujii et al. |

*Primary Examiner* — Yong Chu
(74) *Attorney, Agent, or Firm* — Steven A. Owen

(57) ABSTRACT

An MHT reactor is added to a DMT process to eliminate the majority of the DMT/MHT recycle back to the DMT reactor, allowing for an increase in capacity to the DMT reactors.

6 Claims, 2 Drawing Sheets

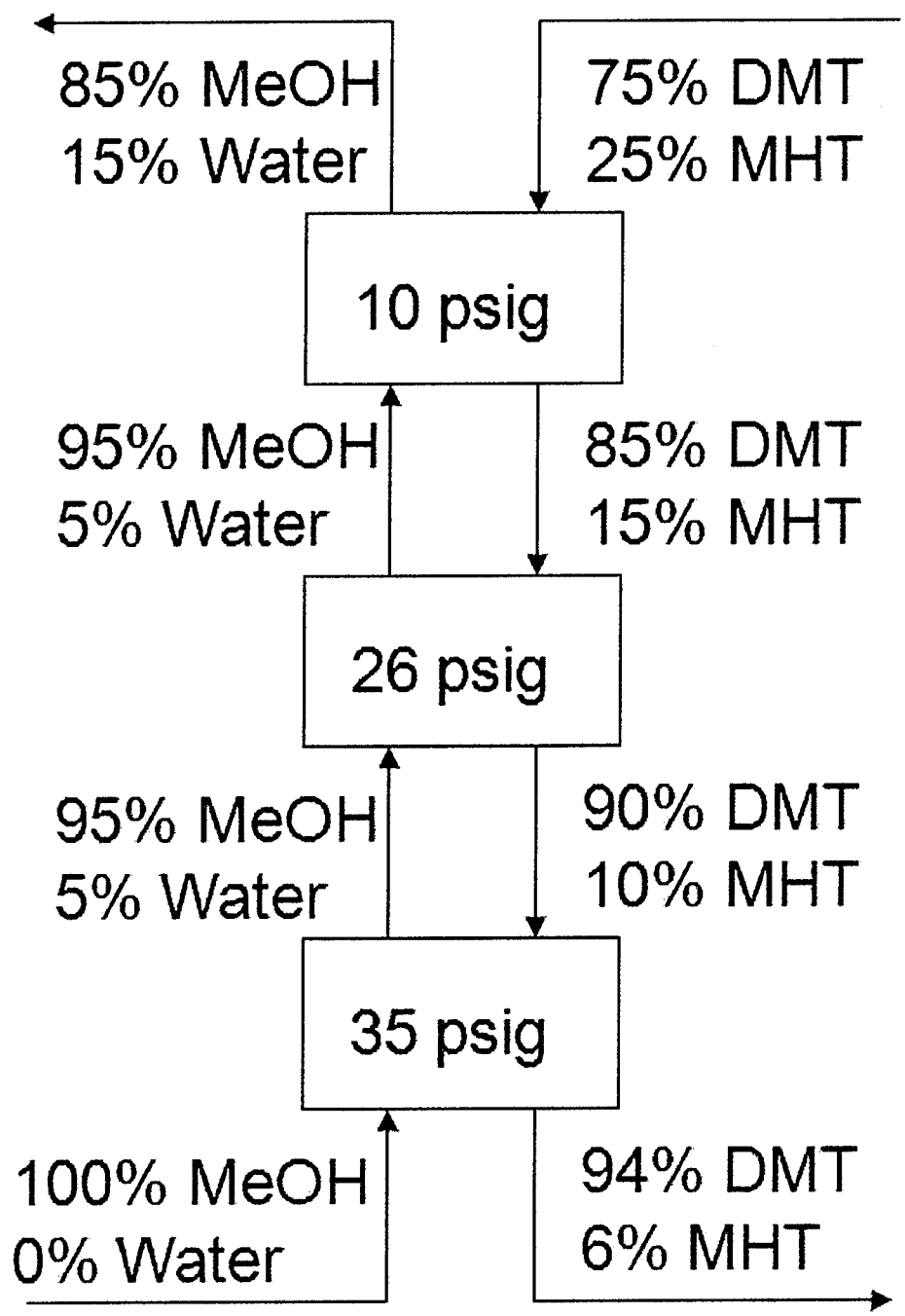
Figure 2. MHT Reactor: Three Stage Model

ADDITION OF A METHYL HYDROGEN TEREPHTHALATE REACTOR TO A DIMETHYL TEREPHTHALATE PROCESS

RELATED APPLICATIONS

This application claims the priority benefit of U.S. Provisional Pat. App. Ser. No. 61/152,277 filed Feb. 13, 2009, the entire disclosures of which are incorporated herein by reference.

FIELD OF INVENTION

The present invention relates to a process by where DMT (Dimethyl Terephthalate) is obtained from an MHT (1,4-Benzenedicarboxylic acid, 1-methyl ester or Methyl Hydrogen Terephthalate) rich stream. More specifically, the present invention relates to a process by which a DMT is obtained from an MHT rich stream through the use of an MHT reactor zone which comprises an MHT reactor.

BACKGROUND OF THE INVENTION

At least two technical problems were solved by the addition of an MHT(1,4-Benzenedicarboxylic acid, 1-methyl ester or Methyl hydrogen terephthalate) reactor in a DMT process. The technical problem solved was the ability to provide for a debottlenecking of a DMT plant. The MHT reactor eliminated the majority of the DMT/MHT recycle back to the DMT reactor in a DMT plant. This can allow for a 20-40% capacity increase on the DMT reactors. DMT is generally produced via the following reactions:

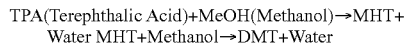

TPA(Terephthalic Acid)+MeOH(Methanol)→MHT+
Water MHT+Methanol→DMT+Water

Other Potential Benefits of the MHT Reactor Design are Listed as Follows:
  Minimize natural gas usage per pound of DMT.
  Able to increase slurry feed rate to DMT reactors. Debottleneck DMT reactors by reducing recycle to reactors.
  Disturbances in base of product refining column can be shifted to the MHT reactor instead of causing significant disturbances to DMT reactor. This decouples the back end of the process from the front end.
  MHT reactor can process additional MHT without causing a large recycle stream of high MHT material.
  The DMT plant's reactors can be shutdown without shutting down the plant's distillation train.

SUMMARY OF THE INVENTION

In one embodiment of the invention, a process to produce a DMT rich stream comprising contacting in an MHT reactor zone an MHT rich stream comprising MHT and DMT with methanol to produce the DMT rich stream and a methanol rich stream.

These objects, and other objects, will become more apparent to others with ordinary skill in the art after reading this disclosure.

BRIEF DESCRIPTION OF THE DRAWINGS

FIG. 2 is schematic illustration of one embodiment of the invention disclosed in the example section.

DETAILED DESCRIPTION OF THE INVENTION

Figure 1:
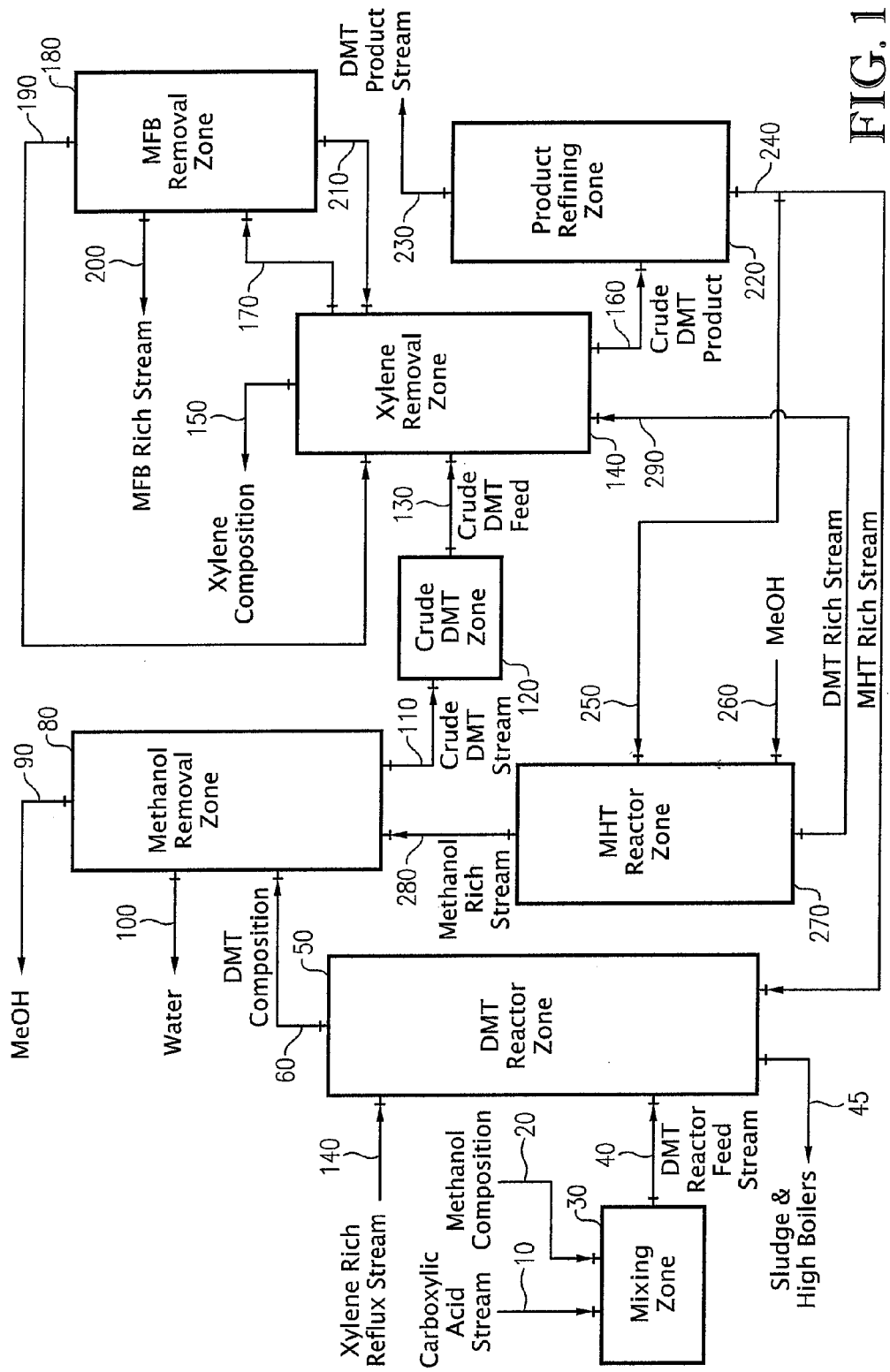
FIG. 1 is a schematic of the inventive process for the production of a DMT product stream 230 wherein a MHT reactor zone 270 can be utilized to produce a DMT rich stream 290 from a MHT rich stream 240.

The present invention may be understood more readily by reference to the following detailed description of preferred embodiments of the invention and the Examples included herein and to the Figures and their previous and following description.

Before the present compounds, compositions, articles, devices, and/or methods are disclosed and described, it is to be understood that this invention is not limited to specific synthetic methods, specific processes, or to particular apparatuses, as such may, of course, vary. It is also to be understood that the terminology used herein is for the purpose of describing particular embodiments only and is not intended to be limiting.

In this specification and in the claims, which follow, reference will be made to a number of terms which shall be defined to have the following meanings:

As used in the specification and the appended claims, the singular forms "a," "an" and "the" include plural referents unless the context clearly dictates otherwise. Thus, for example, reference to a catalyst removal zone includes one or more catalyst removal zones.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. "Optional" or "optionally" means that the subsequently described event or circumstance may or may not occur, and that the description includes instances where said event or circumstance occurs and instances where it does not. For example, the phrase "optionally heated" means that the material may or may not be heated and that such phrase includes both heated and unheated processes. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

In the DMT(Dimethyl Terephthalate) process as shown in FIG. 1, a carboxylic acid stream 10 and a methanol composition stream 20 are sent to a mixing zone 30 to produce a DMT reactor feed stream 40 comprising TPA(terephthalic acid) and methanol. However, it should be noted that other carboxylic acid besides TPA can be used. Examples of suitable carboxylic acids include, but are not limited to, terephthalic acid, isophthalic acid, naphthalene dicarboxylic acid, and mixtures thereof. The DMT reactor feed stream 40 is fed to a DMT reactor zone 50 to produce a DMT composition 60 comprising DMT and Methanol. The DMT reactor zone 50 comprises at least one DMT reactor capable of converting a portion of TPA and methanol to the DMT composition 60. A sludge and high boiler stream via conduit 45 is also produced from the DMT reactor zone 50. In an embodiment of the invention, the DMT reactor zone 50 comprises at least one bubble column reactor.

To increase the reaction time of the MHT in the DMT reactor, a Xylene rich reflux stream 140 comprising xylene is maintained on the DMT reactor in the DMT reactor zone 50.

The DMT composition 60 produced in the reactor is fed directly to a methanol removal zone 80. In the methanol removal zone 80 a portion of methanol in the DMT composition 60 is removed overhead via conduit 90 and a portion of water in the DMT composition 60 is removed in the sidedraw via conduit 100. Some methanol may be in conduit 100 as well.

In an embodiment of the invention the methanol removal zone 80 comprises at least one distillation column. In another embodiment of the invention, the methanol removal zone 80 comprises at least three distillation columns.

A crude DMT stream 110 exits the methanol removal zone and optionally enters the Crude DMT zone 120. The Crude DMT zone 120 comprises at least one crude DMT tank.

The crude DMT feed 130 from the Crude DMT Zone 120 or the crude DMT stream 110 is fed to a Xylene Removal Zone 140. In the Xylene Removal Zone 140 a portion of the Xylene in the crude DMT feed 130 or the crude DMT stream 110 is removed overhead via conduit 150. A sidedraw stream 170 is also removed from the Xylene Removal Zone 140 via conduit 170. The sidedraw stream 170 comprises DMT, Xylene, and MFB (Methyl Formyl Benzoate.) Most of the impurities in the crude feed 130 are concentrated in this stream and fed to a MFB removal zone 180. Conduit 160 from the Xylene Removal Zone 140 is feed to the product Refining Zone 220.

The MFB (Methyl Formyl Benzoate) removal zone 180 takes feed from the Xylene Removal Zone via conduit 170 and produces an MFB rich stream 200. In an embodiment of the invention, the MFB Removal Zone 180 comprises at least one distillation column. In the MFB Removal Zone 180 a portion of the MFB in conduit 170 is removed via conduit 200. Both Conduit 190 and 210 are recycled back to the Xylene Removal Zone 140.

The Product Refining Zone 220 separates a portion of the MHT from stream 160 to form the DMT product 230. In an embodiment of the invention, the DMT product stream 230 comprises DMT in an amount greater than 50% by weight DMT. In another embodiment of the invention, the DMT product stream 230 comprises DMT in an amount greater than 70% by weight DMT. In another embodiment of the invention, the DMT product stream 230 comprises DMT in an amount greater than 90% by weight DMT. The MHT Rich Stream 240 also exits the Product Refining Zone via conduit 240. The MHT Rich Stream 240 comprises MHT. In another embodiment of the invention, the MHT Rich Stream 240 comprises MHT in a range from about 10% MHT to about 35% MHT by weight. In another embodiment of the invention, the MHT Rich Stream 240 comprises MHT in a range from 5% MHT to about 50% MHT. In a typical DMT plant MHT rich stream 240 has been returned to the DMT Reactor Zone 50 where the MHT to DMT reaction is completed. The addition of an MHT reactor zone 270 has altered the operation of the MHT rich stream 240 recycle. In the disclosed process, a portion of the MHT rich stream 240 from the Product Refining Zone 220 are fed to the MHT Reactor Zone 270 along with a stream comprising methanol via conduit 260 to complete the MHT to DMT reaction. In another embodiment of the invention, at least 10% of the MHT Rich Stream 240 is fed to the MHT Reactor Zone 270. In another embodiment of the invention, at least 20% of the MHT Rich Stream 240 is fed to the MHT Reactor Zone 270. In another embodiment of the invention, at least 30% of the MHT Rich Stream 240 is fed to the MHT reactor zone 270. In another embodiment of the invention, at least 40% of the MHT Rich Stream 240 is fed to the MHT Reactor Zone 270. In another embodiment of the invention, at least 50% of the MHT Rich Stream 240 is fed to the MHT Reactor Zone 270. In another embodiment of the invention, at least 60% of the MHT Rich Stream 240 is fed to the MHT Reactor Zone 270. In another embodiment of the invention, at least 70% of the MHT Rich Stream 240 is fed to the MHT Reactor Zone 270. In another embodiment of the invention, at least 80% of the MHT Rich Stream 240 is fed to the MHT Reactor Zone 270. In another embodiment of the invention 100% of the MHT Rich Stream 240 is fed to the MHT Reactor Zone 270. In yet still another embodiment of the invention 100% of the MHT Rich Stream 240 is recycled back to the DMT Reactor Zone 50. The MHT Reactor Zone 270 comprises at least one MHT reactor suitable to convert at least a portion of MHT to DMT in the MHT Rich Stream 240. The outflows from MHT Reactor Zone 270 are a Methanol Rich Stream 280 and a DMT Rich Stream 290. The methanol rich stream 280 is sent to the Methanol Removal Zone 80. The DMT Rich Stream 290 is sent to the Xylene Removal Zone 140. In an embodiment of the invention the MHT Reactor Zone 270 comprises at least one MHT reactor that is a bubble column. In another embodiment of the invention, in the MHT Reactor Zone 270 at least one MHT reactor comprises internal trays that range from 2 to 12 trays. In another embodiment of the invention, the open area on the trays range from about 10 to about 30%. In yet another embodiment of the invention, at least one MHT reactor in the MHT reactor zone 270 comprises at least one sieve tray.

It should be appreciated that the process zones previously described can be utilized in any other logical order to produce the DMT product stream 230. It should also be appreciated that when the process zones are reordered that the process conditions may change.

EXAMPLES

An Embodiment of this invention can be further illustrated by the following examples of preferred embodiments thereof, although it will be understood that these examples are included merely for purposes of illustration and are not intended to limit the scope.

I. Theoretical (Before Start-Up, Lab Testing)

As the MHT reactor concept was developed in the lab, initial experiments were run to determine optimum temperature, pressure and time conditions for the new reactor. Initial lab testing was performed at 10 psig. Based on these experiments, the optimum reaction temperature was determined to be 240 deg C. and the optimum reaction time was one hour.

Once the concept had been confirmed in the lab, the detailed design phase of the MHT reactor was begun. During this development, further lab testing was done to verify the staging in the reactor. With a liquid full reactor (75% level), the residence time in the reactor was estimated to be around three hours. The reactor Was divided into three stages, each with a residence time of one hour to validate the assumptions around the MHT reactor design. The pressure for each test was varied based on a top pressure of 10 psig. The liquid height above each stage was calculated, resulting in a first stage run at 10 psig, a second stage operating at 26 psig and a final stage under 35 psig of pressure. The three stages in the reactor can be depicted by FIG. 2

As the DMT/MHT stream progresses down through the reactor, the MHT composition decreases. Similarly, as the methanol travels up the reactor, it picks up water from the MHT and methanol reaction, thereby decreasing the methanol purity at each higher stage. Lab testing was done to validate these three stages. Each of the three tests was performed at 240 deg C. for one hour. The feed rate assumptions in the lab were an initial DMT/MHT feed of 40 gpm and a methanol feed of 5 gpm. At these conditions, the expected conversion in the reactor was 75%.

II. Example in a Production Facility

In a production facility, the current material balance has about 22 gpm (ranging from 10-50 gpm) of MHT Rich Stream being fed to the reactor with a composition of about 12.5% MHT. The methanol flow is about 8 gpm (ranging from 5-15 gpm) and reactor temperatures from top to bottom range from 220 to 230 deg C. The top pressure on the reactor can be run as high as 10 psig, but has operated at about 9 psig, with the base pressure being about 35 psig as was expected. Conversion is about 84% in this example, resulting in a DMT stream in the base with about 2% MHT.

We claim:

1. A process to produce a DMT rich stream comprising:
   (a) contacting a DMT reactor feed stream in a DMT reactor zone to form a DMT composition,
   (b) contacting said DMT composition in a methanol removal zone to form a crude DMT stream,
   (c) contacting said crude DMT stream in a xylene removal zone to form a crude DMT product,
   (d) contacting said crude DMT product in a product refining zone to form an MHT rich stream,
   (e) contacting in a separate MHT reactor zone said MHT rich stream comprising MHT and DMT with methanol to produce said DMT rich stream and a methanol rich stream.

2. The process according to claim 1 wherein said MHT reactor is a bubble column.

3. The process according to claim 1 wherein said MHT rich stream comprises MHT in a range from about 10% by weight to about 50% by weight.

4. The process according to claim 1 wherein said MHT rich stream comprises MHT in a range from about 5% by weight to about 50% by weight.

5. The process according to claim 2 wherein said bubble column comprises trays ranging from 2 to 12 trays.

6. The process according to claim 5 wherein said bubble column comprises at least one sieve tray.

* * * * *